United States Patent [19]

Schmid et al.

[11] 4,308,253

[45] * Dec. 29, 1981

[54] NOVEL ORAL COMPOSITIONS FOR THE CARE OF THE MOUTH AND TEETH

[75] Inventors: Hans Schmid, Muttenz; Hans R. Mühlemann, Zürich, both of Switzerland

[73] Assignee: Gaba AG, Basel, Switzerland

[*] Notice: The portion of the term of this patent subsequent to Aug. 26, 1997, has been disclaimed.

[21] Appl. No.: 99,026

[22] Filed: Nov. 30, 1979

Related U.S. Application Data

[63] Continuation of Ser. No. 681,343, Apr. 28, 1976, Pat. No. 4,219,541.

[30] Foreign Application Priority Data

Apr. 28, 1975 [CH] Switzerland ............... 5386/75

[51] Int. Cl.³ ............................... A61K 7/22
[52] U.S. Cl. ................................ 424/54
[58] Field of Search ................. 424/54, 246

[56] References Cited

FOREIGN PATENT DOCUMENTS 4914M 3/1967 France ........................ 424/246
1124285 8/1968 United Kingdom ........ 424/246
1385318 2/1975 United Kingdom ........ 424/246

Primary Examiner—Frederick E. Waddell
Attorney, Agent, or Firm—Wenderoth, Lind & Ponack

[57] ABSTRACT

An oral composition for the care of the mouth and teeth which contains as an active ingredient, a compound of the formula:

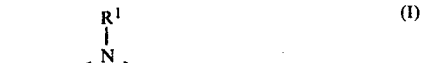

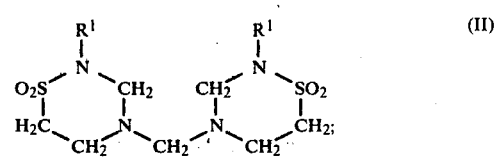

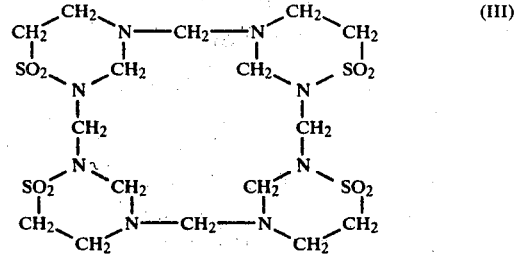

in which $R^1$ and $R^2$ in formulas I and II, may be the same or different and are selected from the group consisting of methyl, ethyl, chloroethyl, hydroxyethyl, aminoethyl, carbethoxymethyl, n-propyl, isopropyl, n-butyl, isobutyl, 1-methylpropyl, t-butyl, hexyl, cyclohexyl, methylcyclohexyl, benzyl, phenyl, chlorophenyl, methoxyphenyl, chloronitrophenyl or dimethylnitrophenyl.

4 Claims, No Drawings

NOVEL ORAL COMPOSITIONS FOR THE CARE OF THE MOUTH AND TEETH

This application is a continuation application of application Ser. No. 681,343, filed Apr. 28, 1976, now U.S. Pat. No. 4,219,541.

The present invention concerns novel oral compositions for the care of the mouth and teeth which inhibit plaque formation, paradentosis and to a lesser extent caries.

As is well known, the purpose of oral compositions for the care of the mouth and teeth is to contribute by virtue of their cleansing action to oral hygiene and hence to the health of the teeth and gums. It has also proved advantageous for oral compositions to possess in addition to this cleansing effect specific properties which prevent or combat pathlogical oral conditions. Compositions which prevent caries and paradental diseases belong to this class, as do those more recent ones which inhibit the formation of bacterially contaminated plaque.

Plaque is of course a significant causal factor in the above oral conditions and is thus of central significance in their aetiology. Films on the teeth consist of polysaccharides, but first and foremost of dextrans which are the metabolic products of the plaque bacteria (principally streptococci and lactobacteria) and also form a substrate or framework which harbours these bacteria. Although sugars are the usual nutrient source of plaque bacteria, the polysaccharides in the plaque represent a nutrient reserve which is decomposed to short-chain organic acids such as lactic acid, pyruvic acid etc. These then attack the tooth enamel at pH values as high as 5.5 or 5.

In addition, the toxins liberated by the plaque bacteria cause inflammatory conditions such as paradentosis. Another cause of paradentosis is the mechanical irritation of the gums provoked for example by tartar which forms particularly on the cervix dentis as a result of calcification of plaque and is a crystalline conglomerate incorporating dead bacteria. The irritant effect of food and individual sensitivity also contribute to the development of paradentosis.

If the tartar extends down to the gum and into the gingival trough, the gum becomes inflamed and draws back. The gingival trough so formed is a source of infection from which the bone is attacked. The bone then also draws back, thus exposing the cervix dentis and causing the tooth to become loose.

If the mouth is sterile so that no plaque can form, no caries or paradentosis can occur either. Efforts have therefore already been made to combat plaque and the conditions which result from it with antibacterial agents. Compounds of the biguanide class have been used as antibacteriants. One example is 1,6-di-(4'-chlorophenyl-diguanido)-hexane, also called chlorhexidine, which has the formula:

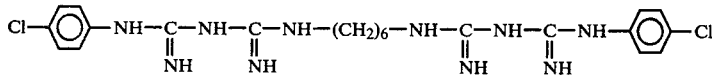

Frequent and regular use of chlorhexidine, as is usually the case with oral compositions, leads in practice to disadvantages such as a temporary neutralisation of the sense of taste and colouration of the teeth and fillings. Hence oral compositions containing chlorhexidine are practically unusable.

It has now been discovered however that it is possible to prepare oral compositions for the care of the mouth and teeth which do not suffer from this disadvantage, if compounds of the following formula are used as antibacteriants:

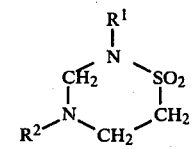

wherein $R^1$ and $R^2$, which may be the same of different, are hydrogen atoms, alkyl groups having 1 to 8 carbon atoms, cycloalkyl radicals, aralkyl radicals or aromatic or heterocyclic groups, whereby both $R^1$ and $R^2$ may be substituted. The production of these compounds is described in Swiss Pat. No. 482,713.

The radicals $R^1$ and $R^2$ may be substituted by e.g. halogen, hydroxyl, amino, acylamido, optionally esterified carboxyl, alkoxy or nitro groups. $R^1$ and/or $R^2$ may also be methylene groups which are bound in turn to a second perhydro-1,2,4-thiadiazine-1,1-dioxide ring.

In this way compounds of the formula:

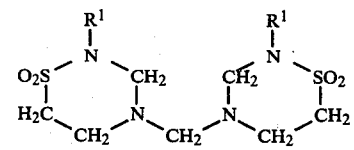

or of the formula:

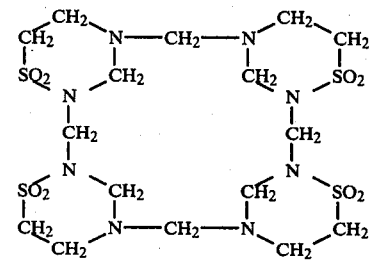

result.

$R^1$ and $R^2$ may also for example be methyl, ethyl, chloroethyl, hydroxyethyl, aminoethyl, carbethoxymethyl, n-propyl, isopropyl, n-butyl, isobutyl, 1-methylpropyl, t-butyl, hexyl, cyclohexyl, methylcyclohexyl, benzyl, phenyl, chlorophenyl, methoxyphenyl, chloronitrophenyl or dimethylnitrophenyl.

Compounds of formula II are particularly preferred since they possess a remarkably low toxicity, and in particular the compound of formula II, in which $R^1$ is hydrogen, and those compounds of formula I, in which $R^1$ and $R^2$ are both cyclohexyl or n-butyl or in which one of the symbols $R^1$ and $R^2$ is phenyl and the other n-butyl are preferred ones.

Compounds which can be used in accordance with the invention are for instance:

(1) 4-n-butyl-2-phenyl-perhydro-1,2,4-thiadiazine-1,1-dioxide
(2) 2,4-dicyclohexyl-perhydro-1,2,4-thiadiazine-1,1-dioxide
(3) 2,4-di-n-butyl-perhydro-1,2,4-thiadiazine-1,1-dioxide
(4) 4,4'-methylene-bis-(perhydro-1,2,4-thiadiazine-1,1-dioxide)
(5) the compound of formula III
(6) 4,4'-methylene-bis-(2-propyl-perhydro-1,2,4-thiadiazine-1,1-dioxide)
(7) 4,4'-methylene-bis-(2-butyl-perhydro-1,2,4-thiadiazine-1,1-dioxide)
(8) 4,4'-methylene-bis-[2-(p-chlorophenyl)-perhydro-1,2,4-thiadiazine-1,1-dioxide]
(9) 4-n-butyl-2-(p-chlorophenyl)-perhydro-1,2,4-thiadiazine-1,1-dioxide
(10) 4-n-propyl-2-(p-chlorophenyl)-perhydro-1,2,4-thiadiazine-1,1-dioxide
(11) 2,4-diphenyl-perhydro-1,2,4-thiadiazine-1,1-dioxide
(12) 4-ethyl-2-(p-chlorophenyl)-perhydro-1,2,4-thiadiazine-1,1-dioxide
(13) 4-methyl-2-(p-chlorophenyl)-perhydro-1,2,4-thiadiazine-1,1-dioxide
(14) 4-($\beta$-diethylaminoethyl)-2-phenyl-perhydro-1,2,4-thiadiazine-1,1-dioxide
(15) 4-cyclohexyl-2-phenyl-perhydro-1,2,4-thiadiazine-1,1-dioxide
(16) 4-n-pentyl-2-phenyl-perhydro-1,2,4-thiadiazine-1,1-dioxide
(17) 4-ethoxycarbonylmethyl-2-phenyl-perhydro-1,2,4-thiadiazine-1,1-dioxide
(18) 4-methyl-perhydro-1,2,4-thiadiazine-1,1-dioxide.

The compounds of formula I are very suitable for use against plaque and thus for the prevention of paradentosis, although they are less effective against caries. This is a significant difference compared with the fluorides which were introduced to combat caries. The inorganic fluorides do not combat plaque, whereas the aminofluorides do.

The products of the invention by means of which an antimicrobial compounds described above are applied to the mouth are principally pastes, gels, rinses, liquid concentrates which are diluted before use to give rinses (mouth washes), sprays, tooth powders, chewing tablets, chewing gums and sucking tablets. These preparations contain substances suited to the particular way in which the preparation is administered and intended to enable the above antimicrobial compounds to be applied to the mouth in the most aggreeable way and in the most effective form.

Toothpastes consist basically of a mixture comprising abrasives, binders and softeners, humectants, tensides, flavouring agents and aroma agents and preservatives as well as other additives where necessary.

The following may be used as abrasives: alkaline earth phosphates, e.g. dicalcium phosphate dihydrate, dicalcium phosphate anhydride, tricalcium phosphate; insoluble alkali metaphosphates, finely ground or colloidal silicon dioxides, aluminum oxide hydrates, aluminum silicates, aluminum magnesium silicates and alkaline earth carbonates. As is known from the prior art, suitable synthetic compounds are also added in powder form to paste preparations. These abrasives and fillers are usually added in amounts of from 20 to 60%, preferably 30 to 45%, based on the finished paste preparation.

The binders are gelling agents of natural or synthetic origin. The following representative compounds are suitable: water-soluble alginates, carragheenates, guar gum, tragacanth and water-soluble cellulose ethers such as methyl cellulose, hydroxyalkyl cellulose and carboxymethyl cellulose. Other thickeners are water-soluble salts of polyacrylic acids (Carbopols ®, Aerosils ® and bentonites. In general the toothpastes contain 0.5 to 10%, preferably 0.5 to 4%, of these swelling agents.

The softeners and humectants are polyhydric alcohols such as glycerol, sorbitol, mannitol, glucose syrup, polyethylene glycols, polypropylene glycols and polyvinyl pyrrolidone.

The addition of tensides (detergents) is appropriate in cases in which a foaming composition is required. Anionic, non-ionic and/or cationic detergents can be added. On account of its better properties as regards taste, the former group of compounds is preferred. This group as a rule possesses the ability to foam very well. The following classes of compounds can for instance be used: fatty alcohol sulphates, sodium lauryl ether sulphates and the sodium, potassium and ethanolamine salts of N-lauroyl, N-myristoyl and N-palmitoyl sarcosine. Other compounds are protein-fatty acid condensates, imidazoline derivatives, polyoxyethylene esters, fatty amines with the betaine structure (e.g. Tegobetaines ® made by Goldschmid & Co.), sucrose esters, amine oxides and ethers of polyethylene glycols and linear alcohols.

Saccharin, quaternary ammonium saccharinates, cyclamates, coumarin and vanillin are suitable for use as flavouring agents while mixtures of the essential oils usually used as aroma agents may be added. The main aroma agents are peppermint oil, spearmint oil, aniseed oil, menthol and anethol as well as citrus oil, methyl salicylate etc.

Liquid compositions consist of an aqueous, alcoholic or preferably aqueous-alcoholic solution of the antibacteriants described above. The conventionally employed additives are also used herein, e.g. flavouring and aroma agents, emulsifiers and wetting agents, glycerol, sorbitol, xylitol and drug tinctures.

Gel compositions contain a swollen mass of natural or synthetic hydrocolloids as the carrier. Methyl cellulose, hydroxyalkyl cellulose, carboxymethyl cellulose, insoluble and swellable salts of polyacrylic acids, alginates, carragheenates and guar gum are suitable. Besides the antibacteriants of the present invention, flavouring and aroma agents, humectants and/or small amounts of pigments may be added to a gel base.

Tooth powders are intimate mixtures of the active substances with carriers like those in some toothpastes. These carriers are alkaline earth phosphates, aluminium oxides, aluminium silicates and aluminium magnesium silicates, alkaline earth carbonates, finely ground or colloidal silicon dioxide and insoluble alkali metaphosphates. As a rule, aroma and flavouring agents, emulsifiers and detergents are also added.

Compositions in tablet form contain the active ingredients within suitable carriers. For sucking tablets water-soluble carriers are suitable, e.g. saccharose in combination with gum arabic, gelatine, methyl cellulose and/or carboxymethyl cellulose. Non-cariogenic polyalcohols are preferred however—xylitol, sorbitol and mannitol being particularly suitable. The addition of high molecular weight polyethylene glycols (e.g. carbowax 6000) is also customary with this kind of composition.

Chewing tablets as a rule contain no disintegrating agents since they are supposed to only disintegrate or dissolve slowly. The main ingredients are saccharose, glucose, lactose or the preferred, non-cariogenic sugars such as xylitol, mannitol and sorbitol. The tablets contain relatively large amounts of binders.

The mouth sprays are pleasantly aromatized, usually aqueous-alcoholic solutions which are contained in pressure cans together with the usual quantity of a suitable propellant.

The present invention will now be illustrated by means of Examples, without being limited thereto.

Example 1

| Toothpaste | % |
|---|---|
| 2,4-di-n-butyl-perhydro-1,2,4-thiadiazine-1,1-dioxide | 1.00 |
| methyl cellulose | 1.800 |
| glycerol | 20.000 |
| dicalcium phosphate dihydrate | 30.000 |
| dicalcium phosphate anhydride | 5.000 |
| Na lauryl sarcosinate | 2.000 |
| saccharin | 0.100 |
| preservative (hydroxybenzoic acid methyl ester) | 0.105 |
| aroma agents | 1.500 |
| water | to 100.000 |

Example 2

| Toothpaste | % |
|---|---|
| 4,4'-methylene-bis-(perhydro-1,2,4-thiadiazine-1,1-dioxide) | 0.500 |
| carragheenate | 1.600 |
| sorbitol | 12.000 |
| dicalcium phosphate dihydrate | 40.000 |
| sodium lauryl sulphate | 1.500 |
| saccharin | 0.080 |
| aroma agents | 1.400 |
| preservative | 0.200 |
| titanium dioxide | 1.000 |
| water | to 100.000 |

Example 3

| Transparent toothpaste | % |
|---|---|
| compound of formula III | 2.000 |
| silicon dioxide, microfine | 25.000 |
| glycerol | 55.000 |
| silicic acid, colloidal (Aerosil) | 2.000 |
| alkyldimethylamine oxide | 1.750 |
| aroma agents | 1.200 |
| water | to 100.000 |

These toothpastes can be produced as follows.

The methylcellulose or the carragheenate is dissolved together with the preservative in part of the water to form a slime. The active substance dissolved in the remaining water is then added, the glycerol or sorbitol is added, then the abrasives, and finally the aroma, wetting and foaming agents are incorporated. The resulting mixture is well blended in a suitable mixer and if necesssary homogenised in a colloid mill.

Transparent toothpastes are prepared by mixing the glycerol and colloidal silicic acid, incorporating the silicon dioxide and mixing the resulting paste with the detergent, the aroma agents and the remaining water.

Example 4

| mouth rinse | % |
|---|---|
| perhydro-1,2,4-thiadiazine-1,1-dioxide | 0.500 |
| aroma agents | 0.070 |
| sodium saccharate | 0.050 |

Example 4 -continued

| mouth rinse | % |
|---|---|
| polyoxyethylene sorbitan monoaleate (Emulsifier) | 1.000 |
| ethanol | 20.000 |
| water | to 100.000 |

The active ingredient is dissolved in the amount of alcohol given in the recipe. To the resulting solution is added a solution of the emulsifier, the aroma agents and the saccharin in half the water. The preparation of the composition is completed by adding the remaining water. This rinse can be used without diluting it.

Example 5

| Tooth powder | % |
|---|---|
| perhydro-1,2,4-thiadiazine-1,1-dioxide | 2.000 |
| dicalcium phosphate dihydrate | 70.850 |
| dicalcium phosphate anhydride | 10.000 |
| aluminium oxide | 10.000 |
| disodiumhydrogen phosphate | 4.000 |
| sodium salt of fatty alcohol sulphate | 2.000 |
| sodium saccharate | 0.150 |
| aroma agents | 1.000 |
| | 100.000 |

Example 6

| Sucking tablets | % |
|---|---|
| perhydro-1,2,4-thiadiazine-1,1-dioxide | 2.000 |
| xylitol | 20.000 |
| sorbitol | 73.800 |
| magnesium stearate | 4.000 |
| aroma agents | 0.200 |
| | 100.000 |

The active substance and the aroma agents are dissolved in ethanol, the carriers, i.e. xylitol and sorbitol, moistened with this solution, the resulting moist material passed through a sieve and carefully dried. Magnesium stearate is mixed into the resulting dry granular solid which is then pressed into hard tablets.

We claim:

1. A toothpaste for the care of the mouth or teeth, for preventing plaque formation, paradentosis or caries consisting essentially of an effective antibacterial amount for preventing plaque formation, paradentosis or caries in the mouth of a compound of the formula:

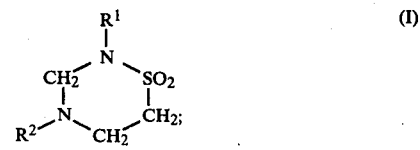

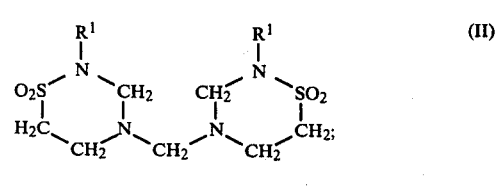

or

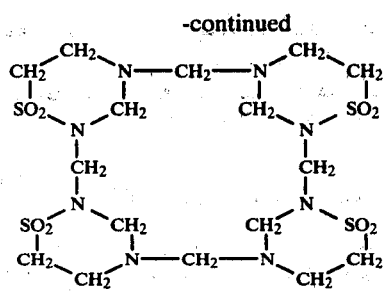

in which $R^1$ and $R^2$ in formulas I and II, may be the same or different and are selected from the group consisting of methyl, ethyl, chloroethyl, hydroxyethyl, aminoethyl, carbethoxymethyl, n-propyl, isopropyl, n-butyl, isobutyl, 1-methylpropyl, t-butyl, hexyl, cyclohexyl, methylcyclohexyl, benzyl, phenyl, chlorophenyl, methoxyphenyl, chloronitrophenyl or dimethylnitrophenyl; abrasives in an amount of 20–60 percent, said abrasives selected from the group consisting of dicalcium phosphate dihydrate, dicalcium phosphate anhydride, tricalcium phosphate, insoluble alkali metaphosphates, finely ground or colloidal silicon dioxides, aluminum oxide hydrates, aluminium silicates, aluminium magnesium silicates and alkaline earth carbonates; binders in an amount of 0.5 to 10 percent, said binders selected from the group consisting of water-soluble alginates, carragheenates, guar gum, tragacanth and water-soluble cellulose ethers selected from methyl cellulose, hydroxyalky cellulose and carboxymethyl cellulose, water-soluble salts of polyacrylic acids, Aerosils and bentonites; an effective amount of an anionic, nonionic and cationic detergent and the remainder being essentially water.

2. A toothpaste according to claim 1 consisting essentially of the following ingredients:

|  | % |
| --- | --- |
| 2,4-di-n-butyl-perhydro-1,2,4-thiadiazine-1,1-dioxide | 1.000 |
| methyl cellulose | 1.800 |
| glycerol | 20.000 |
| dicalcium phosphate dihydrate | 30.000 |
| dicalcium phosphate anhydride | 5.000 |
| Na lauryl sarcosinate | 2.000 |
| saccharin | 0.100 |
| preservative (hydroxybenzoic acid methyl ester) | 0.150 |
| aroma agents | 1.500 |
| water | to 100.00 |

3. A mouth rinse consisting essentially of the following ingredients:

|  | % |
| --- | --- |
| perhydro-1,2,4-thiadiazine-1,1-dioxide | 0.500 |
| aroma agents | 0.070 |
| sodium saccharate | 0.050 |
| polyoxyethylene sorbitan monooleate (Emulsifier) | 1.000 |
| ethanol | 20.000 |
| water | to 100.00 |

4. A sucking tablet consisting essentially of the following ingredients:

|  | % |
| --- | --- |
| perhydro-1,2,4-thiadiazine-1,1-dioxide | 2.000 |
| xylitol | 20.000 |
| sorbitol | 73.800 |
| magnesium stearate | 4.000 |
| aroma agents | 0.200 |
|  | 100.000 |

* * * * *